(12) United States Patent
Pelet et al.

(10) Patent No.: US 9,526,700 B2
(45) Date of Patent: *Dec. 27, 2016

(54) COMPOSITION FOR INACTIVATING AN ENVELOPED VIRUS

(71) Applicant: VIROBLOCK S.A., Geneva (CH)

(72) Inventors: Thierry Pelet, Le Lignon (CH); Donald F. H. Wallach, Genèva (CH)

(73) Assignee: VIROBLOCK SA, Plan-les-Ouates (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/543,561

(22) Filed: Nov. 17, 2014

(65) Prior Publication Data
US 2015/0065458 A1 Mar. 5, 2015

Related U.S. Application Data

(63) Continuation of application No. 12/301,381, filed as application No. PCT/IB2007/001286 on May 18, 2007, now Pat. No. 8,889,398.

(60) Provisional application No. 60/801,400, filed on May 19, 2006.

(51) Int. Cl.
| | |
|---|---|
| A61K 31/20 | (2006.01) |
| A61P 31/12 | (2006.01) |
| C12N 7/06 | (2006.01) |
| A61K 9/127 | (2006.01) |
| A61K 31/724 | (2006.01) |
| A61K 47/48 | (2006.01) |
| C12N 7/00 | (2006.01) |
| A61K 45/06 | (2006.01) |

(52) U.S. Cl.
CPC ........... *A61K 9/1271* (2013.01); *A61K 31/724* (2013.01); *A61K 45/06* (2013.01); *A61K 47/48215* (2013.01); *C12N 7/00* (2013.01); *C12N 2760/18863* (2013.01)

(58) Field of Classification Search
CPC .............. A61K 31/724; A61K 2300/00; A61K 47/48215; A61K 9/1271; A61K 9/1272; C12N 2760/18863; C12N 7/00
See application file for complete search history.

(56) References Cited

U.S. PATENT DOCUMENTS

| | | | | |
|---|---|---|---|---|
| 5,561,062 A | * | 10/1996 | Varanelli | A61K 9/1272 424/450 |
| 2005/0015847 A1 | * | 1/2005 | Scheele | A61F 13/104 2/167 |

OTHER PUBLICATIONS

Adam, C.D., et al., "Gel and Liquid-crystal Phase Structures of the Trioxyethylene Glycol Monohexadecyl Ether/Water System," *Faraday Trans I.* 80:789-801, Royal Society of Chemistry (1984).
Aloia, R.C., et al., "Lipid composition and fluidity of the human immunodeficiency virus envelope and host cell plasma membranes," *Proc. Natl. Acad. Sci.* 90:5181-5185, the National Academy of Sciences (1993).

(Continued)

*Primary Examiner* — Savitha Rao
(74) *Attorney, Agent, or Firm* — Chenghua Luo (57) ABSTRACT

The present invention relates generally to the field of prevention of diseases caused by enveloped viruses. More particularly, this invention concerns a composition for inactivating an enveloped virus comprising at least one non phospholipid Lipid Vesicle (nPLV) able to interact with said enveloped virus and an agent that enhances the lipid exchange between said nPLV and the membrane of said enveloped virus.

13 Claims, 2 Drawing Sheets

(56) References Cited

OTHER PUBLICATIONS

Arispe, N. and Doh, M., "Plasma membrane cholesterol controls the cytotoxicity of Alzheimer's disease AβP (1-40) and (1-42) peptides," *FASEB Journal* 16:1526-1536, The Federation of American Societies for Experimental Biology (2002).
Bai, J. and Pagano, R.E., "Measurement of Spontaneous Transfer and Transbilayer Movement of BODIPY-Labeled Lipids in Lipid Vesicles," *Biochemistry* 36:8840-8848, American Chemical Society (1997).
Danthi, P. and Chow, M., "Cholesterol Removal by Methyl-β-Cyclodextrin Inhibits Poliovirus Entry," *Journal of Virology* 78:33-41, the American Society for Microbiology (2004).
Düzgüneş, N., et al., "Delivery of Antiviral Agents in Liposomes," *Methods Enzymol.* 391:351-373, Elsevier Inc. (2005).
Düzgüneş, N., et al., "Liposome-Mediated Therapy of Human Immunodeficiency Virus Type-1 and Mycobaterium Infections," *Journal of Liposome Research* 5:669-691, Marcel Dekker, Inc. (1995).
El Baraka, M., et al., "Non-phospholipid fusogenic liposomes," *Biochim. Biophys. Acta* 1280:107-114, Elsevier Science B.V. (1996).
Greenberg, M.L. and Cammack, N., "Resistance to enfuvirtide, the first HIV fusion inhibitor," *J. Antimicrobial Chemotherapy* 54:333-340, The British Society for Antimicrobial Chemotherapy (2004).
Heerklotz, H., "Triton Promotes Domain Formation in Lipid Raft Mixtures," *Biophys. J.* 83:2693-2701, the Biophysical Society (2002).
Hersberger, M., et al., "Influence of Practicable Virus Inactivation Procedures on Tests for Frequently Measured Analytes in Plasma," *Clin. Chem.* 50:944-946, American Association for Clinical Chemistry (2004).
Khanna, K.V., et al., "Vaginal transmission of cell-associated HIV-1 in the mouse is blocked by a topical, membrane-modifying agent," *Journal of Clinical Investigation* 109:205-211, American Society for Clinical Investigation (2002).
Kilby, J.M. and Eron, J.J., "Novel Therapies Based on Mechanisms of HIV-1 Cell Entry," *New Engl. J. Med.* 348:2228-2238, Massachusetts Medical Society (2003).
Lantzsch, G., et al., "Surface areas and packing constraints in POPC/$C_{12}EOn$ membranes. A time-resolved fluorescence study," *Biophys. Chem.* 58:289-302, Elsevier Science B.V. (1996).
Liao, Z., et al., "Lipid Rafts and HIV Pathogenesis: Host Membrane Cholesterol is Required for Infection by HIV Type 1," *AID Research and Human Retroviruses* 17:1009-1019, Mary Ann Liebert, Inc. (2001).
McLean, L.R. and Phillips, M.C., "Mechanism of Cholesterol and Phosphatidylcholine Exchange or Transfer between Unilamellar Vesicles," *Biochemistry* 12:2893-2900, American Chemical Society (1981).
Mitchell, D.J., et al., "Phase Behaviour of Polyoxyethylene Surfactants with Water," *Faraday Trans. I.* 79:975-1000, Royal Society of Chemistry (1983).
Moscona, A., "Neuraminidase Inhibitors for Influenza," *New. Engl. J. Med.* 353:1363-1373, Massachusetts Medical Society (2005).
Mukherjee, S. and Chattopadhyay, A., "Membrane Organization at Low Cholesterol Concentrations: A Study Using 7-Nitrobenz-2-oxa-1,3-diazol-4-yl-Labeled Cholesterol," *Biochemistry* 35:1311-1322, American Chemical Society (1996).
Ono A. and Freed, E.O., "Plasma membrane rafts play a critical role in HIV-1 assembly and release," *Proc. Natl. Acad. Sci.* 98:13925-13930, the National Academy of Sciences (2001).
Pelet, T., et al., "High throughput screening assay for negative single stranded RNA virus polymerase inhibitors," *J. Virol. Methods* 128:29-36, Elsevier B.V. (2005).

Roberts, P., "Resistance of Vaccinia Virus to Inactivation by Solvent/Detergent Treatment of Blood Products," *Biologicals* 28:29-32, Academic Press (2000).
Rockstroh, J.K. and Mauss, S., "Clinical perspective of fusion inhibitors for treatment of HIV," *J. Antimicrobial Chemotherapy* 53:700-702, The British Society for Antimicrobial Chemotherapy (2004).
Rousso, I., et al., "Palmitoylation of the HIV-1 envelope glycoprotein is critical for viral infectivity," *Proc. Natl. Acad. Sci.* 97:13523-13525, the National Academy of Sciences (2000).
Scheiffele, P., et al., "Influenza Viruses Select Ordered Lipid Domains during Budding from the Plasma Membrane," *J. Biol. Chem.* 274:2038-2044, The American Society for Biochemistry and Molecular Biology, Inc. (1999).
Simons, K. and Ehehalt, R., "Cholesterol, lipid rafts, and disease," *J. Clin. Invest.* 110:597-603, The American Society for Clinical Investigation (2002).
Steck, T.L., et al., "Probing Red Cell Membrane Cholesterol Movement with Cyclodextrin," *Biophys. J.* 83:2118-2125, the Biophysical Society (2002).
Tasitima, K.T. and Carpenter, C.C.J., "Fusion Inhibition—A Major but Costly Step Forward in the Treatment of HIV-1," *N. Engl. J. Med.* 348:2249-2250, Massachusetts Medical Society (2003).
Tuckey, R.C., et al., "Transfer of Cholesterol between Phospholipid Vesicles Mediated by the Steroidogenic Acute Regulatory Protein (StAR)," *J. Biol. Chem.* 277:47123-47128, the American Society for Biochemistry and Molecular Biology (2002).
Ambrose, Z., et al., "Incomplete Protection against Simian Immunodeficiency Virus Vaginal Transnission in Rhesus Macaques by a Topical Antiviral Agent Revealed by Repeat Challenges," *J. Virol.* .82(13):6591-6599, American Society for Microbiology, United States (2008).
Citovsky, V. and Loyter, A., "Fusion of Snedai Virions or Reconstituted Sendai Virus Envelopes with Liposomes or Erythrocyte Membranes Lacking Virus Receptors," *J. Biol. Chem.* 260(22):12072-12077, The American Society of Biological Chemists, Inc., United States (1985).
Fujita, et al., "Methyl-beta cyclodextrin alters the production and infectivity of Sendai virus," *Arch Viol* 156:995-1005, Springer-Verlag, Germany (2011).
Guyader, M., et al., "Role for Human Immunodeficiency Virus Type 1 Membrane Cholesterol in Viral Internalization," *J. Virol.* 76(20):13056-10364, American Society for Microbiology, United States (2002).
Liao, Z., et al., "Lipid Rafts and HIV Pathogenesis: Viron-Associated Cholesterol is required for Fusion and Infection of Susceptible Cells," *AIDS Research and Human Retroviruses* 19(8):675-687, Mary Ann Liebert, Inc., United States (2003) (Abstract Only).
Scheiffele, P., et al., "Influenza Viruses Select Ordered Lipid Domains during Budding from the Plasma Membrane," *J. Biol. Chem.* 274(4):2038-2044, The American Society of Biological Chemists, Inc., United States (1999).
Steck, T.L., et al., "Probing Red Cell Membrane Cholesterol Movement with Cyclodextrin," *Biophysical Journal* 83:2118-2125, The Biophysical Society, United States (2002).
Sun, X. and Whittaker, G.R., "Role for Influenza Virus Envelope Cholesterol in Virus Entry and Infection," *J. Virol.* 77(23):12543-12551, American Society for Microbiology, United States (2003).
White, J. and Helenius A., "pH-dependent fusion between Semliki Forest virus membrane and liposomes," *Proc. Natl. Acad. Sci. USA* 77(6):3273-3277, National Academy of Sciences of the United States, United States (1980).
International Search Report for International Patent Application No. PCT/IB2007/001286, European Patent Office, Rijswijk, Netherlands, mailed May 2, 2008.

* cited by examiner

COMPOSITION FOR INACTIVATING AN ENVELOPED VIRUS

FIELD OF THE INVENTION

The present invention relates generally to the field of prevention of diseases caused by enveloped viruses. More particularly, this invention concerns a composition for inactivating an enveloped virus comprising at least one non phospholipid Lipid Vesicle (nPLV) able to interact with said enveloped virus and an agent that enhances the lipid exchange between said nPLV and the membrane of said enveloped virus.

BACKGROUND OF THE INVENTION

Viruses are packets of genetic material associated with a few virus-specific proteins. They enter selected cells via specific receptors, replicate within these, using the normal cellular machinery and exit most often by destroying their former hosts. Antiviral strategies have employed immunological techniques or drugs inhibiting virus-specific functions. This has been difficult because agents against many viruses also interfere with normal cellular functions. Because viruses have evolved towards a minimal number of virus-specific functions, appropriating normal, cellular functions instead, virus-specific targets are few in number. Since there are a great variety of viruses, an agent targeted to an activity specific to a given virus is unlikely to act equivalently on a different virus. Because the virus genome mutates frequently, viruses commonly develop resistance against specific, previously effective agents, allowing escaping the selective pressures of chemotherapeutic agents. Thus, of the thousands of antivirals tested, only about 40 continue efficacious, of which one half is anti-HIV agents. Combinations of anti-HIV agents are commonly necessary to achieve significant benefit. Similarly, "antigenic shift" mutations occur often after a vaccine has been employed, making the vaccine less protective (a year or so in the case of influenza) and this is a major problem in strategies against a possible influenza pandemic.

Viruses can be grouped into non-enveloped and enveloped viruses. Enveloped viruses are enclosed within a lipoprotein membrane, or envelope. This envelope is derived from the host cell as the virus "buds" from its surface and consists mostly of lipids not encoded by the viral genome. Even though it carries molecular determinants for attachment and entry into target cells, and is essential for the infectivity of enveloped viruses, it is not subject to drug resistance or antigenic shift.

Although virus envelope lipids derive from the host cell plasma membrane, they are deposited in the envelopes at proportions differing from that membrane. For example, the envelope of HIV is enriched in cholesterol (2.5 times) and in sphingomyelin (3 times), both located mainly in the external lamella of the envelope. (Aloia, et al 1993.) The membranes of influenza viruses are similarly enriched (Scheiffele, et al 1999) and the same pattern has been reported for other enveloped viruses. Importantly, it has recently been shown that cholesterol depletion interferes with the infectivity of enveloped viruses (Ono and Freed, 2001; Simons and Ehehalt, 2002). Indeed, the evidence indicates that the envelopes of many enveloped viruses contain phase separated "lipid rafts" enriched in cholesterol thus suggesting that viral envelope lipids may be a target in the arsenal against enveloped viruses.

Since the raft lipids of virus infected cells are synthesized by these cells, use of cell-directed inhibitors, such as the "statins" will exert too much systemic toxicity to be acceptable as "anti-raft agents". Indeed anti-raft strategies will be effective only against extra cellular forms of the virus, when these forms are externally accessible, namely in the naso- and oropharynx and respiratory tract (e.g. influenza), the urogenital tract (e.g. HIV), the skin (e.g. herpes simplex) or deposited on surfaces (fomites).

The fact that cholesterol and other lipids can exchange between the phospholipid lamellae of cellular membranes, as well as liposomes, provides important information. McLean and Phillips (1981) point out that the short "half-time", $T_{1/2}$, 2-3 min, of cholesterol transfer between liposomes indicates collisions between these particles. Steck et al (2002) support this conclusion. They have shown that all the cholesterol transfer from red cells to an acceptor occurs with a $T_{1/2}$~1 sec, depending only of the concentration of the acceptor. They propose an "activation-collision" mechanism, where cholesterol is captured by collision. The $T_{1/2}$ for the transfer of a fluorescent analogue of sphingomyelin between membranes is ~21 sec (Bai and Pagano, 1997) and the "off-rate" $T_{1/2}$, for the transfer of $C_{18}$ fatty acids from oil to water is ~1.3 sec (Small, 2002). In contrast, the $T_{1/2}$ for the transfer of phosphatidyl-choline between liposomes was measured to be ~48 h at 37° C. (McLean and Phillips, 1981).

These data suggest the possibility that enveloped viruses might be inactivated by exposure to phospholipid liposomes. However, phospholipid liposomes are extremely costly, unstable and are unlikely to be available in the quantities needed for prophylaxes. Moreover phospholipid liposomes cannot readily be made with the low cholesterol content required to give net extraction (rather than the two-way exchange) of this lipid and their production requires the use of organic solvents that are a major source of cellular toxicity.

Liposomes can be used to transport drugs for the delivery of pharmaceutical or cosmetic compositions. For example, International Patent Application WO96/12472 (Chinoin Gyógyszer És Vegyészeti Termékek Gyára R T et al.) disclosed a liposomic composition containing, as active ingredient, (−)-N-alpha-dimethyl-N-(2-propynylphenylethylamine) (selegilin) and/or salt thereof. The disclosed composition contains 0.1-40% by weight of selegilin and/or a salt thereof, 2 to 40% by weight of lipids, preferably phospholipids, 0 to 10% by weight of cholesterol, 0 to 20% by weight of an alcohol, 0 to 25% by weight of a glycol, 0 to 3% by weight of an antioxidant, 0 to 3% by weight of a preserving agent, 0 to 2% by weight of a viscosity influencing agent, 0 to 50% by weight of cyclodextrin or a cyclodextrin derivative and 30 to 90% by weight of water. This application also provides the administration of said composition for the treatment of Alzheimer's disease, Parkinson's disease, depression, stroke, motion sickness or myelitis.

It is also known from WO2005030170 (Université Pasteur et al.) a method for initiating the controlled rupture of the membrane of a biocompatible phospholipid liposome, often called a furtive liposome, thereby releasing the liposome content to the environment thereof. A releasing agent, preferably an α-cyclodextrin, is embodied in the form of a biocompatible molecule.

For the reasons described above, the Applicants have explored the advantages of using liposomes such as non phospholipid Lipid Vesicle (nPLV) composed of single-chain poly-(ethylene glycol)-alkyl ethers [(PEG)-alkyl ethers] instead of phospholipid liposomes (Wallach, 1996; Varanelli et al. 1996; Wallach and Varanelli, 1997).

U.S. Pat. No. 5,561,062 (Varanelli et al.) already provides an in vitro method of inactivating enveloped viruses by using paucilamellar lipid vesicles, preferably having non-phospholipids, and preparations useful in accomplishing this inactivation. The method is based on the discovery that paucilamellar lipid vesicles, preferably having non-phospholipids as their primary structural material, can fuse with enveloped virus and that the nucleic acid of the virus denatures shortly after the fusion. Generally, the paucilamellar lipid vesicle is filled with either an oil solution or a water solution, both containing a nucleic acid degrading agent.

An other patent application, EP 1 304 103 A1 (D. F. H Wallach) provides lipid vesicles wherein all said lipids are non phospholipids, as well as their use as vehicle particularly in therapeutic applications such as prevention of AIDS. These non-phospholipid lipid vesicles comprise at least one external stabilized bilayer comprising amongst other a bilayer-modulating lipid chosen from the cholesterol family, an intravesicular aqueous space and at least one intravesicular micro-emulsion particle surrounded by an internal lipid monolayer. Inactivation of the HIV virus is due to the fusion of the non-phospholipid lipid vesicle with the membrane of said virus. This fusogenic property is probably due to the presence of cholesterol in the modulating lipid bilayer and there is no exchange of lipids between said non-phospholipid lipid vesicle containing cholesterol and the membrane of the HIV virus. Fusion between the nPLV described above and the membrane of an enveloped virus is not appropriate for in vivo inactivating said enveloped virus since it needs a long time to take place.

Despite the disclosure of the foregoing patents and patent applications, there remains therefore a need for a new method of inactivating an enveloped virus that is rapid and efficient, in vitro as well as in vivo.

SUMMARY OF THE INVENTION

The present invention concerns a composition for inactivating an enveloped virus characterized in that it comprises at least one non phospholipid Lipid Vesicle (nPLV) able to interact with an enveloped virus and an agent that enhances the lipid exchange between said nPLV and the membrane of said enveloped virus, wherein said nPLV is cholesterol free.

A further object of the present invention is to provide a method for inactivating an enveloped virus comprising interacting said enveloped virus with the composition of the invention so as so as to exchange their lipids.

Still another object of the invention is to provide a pharmaceutical composition comprising a pharmaceutically amount of the composition of the invention, optionally in combination with one or more pharmaceutically acceptable carriers.

Another aspect of the invention provides a method for treating or preventing a disease associated with an enveloped virus in a subject comprising the step of delivering to said subject the pharmaceutical composition of the invention to a location proximate to said enveloped virus.

The invention also contemplates the use of the composition of the invention, in the preparation of a medicament for the treatment or prevention of an enveloped virus-associated disease.

A further object of the present invention is to provide the use of the composition of the invention in the preparation of a large-scale biocompatible disinfectant or of a coating agent.

Other objects and advantages will become apparent to those skilled in the art from a review of the ensuing detailed description, which proceeds with reference to the following illustrative drawings, and the attendant claims.

BRIEF DESCRIPTION OF THE FIGURES

FIG. 2 A shows the synergistic effect of cyclodextrin on the inactivation of an enveloped virus (Sendai virus) by various dilutions of nPLVs (0.02%, 0.05% and 0.1%).

FIG. 2 B shows the direct effect of increasing concentrations of cyclodextrin, in absence of nPLVs, on the inactivation of an enveloped virus (Sendai virus).

DETAILED DESCRIPTION OF THE INVENTION

The present invention relates to a composition for inactivating an enveloped virus comprising at least one non phospholipid Lipid Vesicle (nPLV) able to interact with an enveloped virus and an agent that enhances the lipid exchange between said nPLV and the membrane of said enveloped virus, wherein said nPLV is cholesterol free.

"A" or "an" means "at least one" or "one or more."

As used herein, the terms "liposome" and "lipid vesicle" are used interchangeably to designate a small sphere made of lipid shells enclosing a central cavity mostly composed of an aqueous volume. The lipids are in the form of bimolecular layers, or lamellae, in an onion-like structure.

The terms "unilamellar", "paucilamellar", "multilamellar", as used herein, refer to the number of peripheral bilayers surrounding the central cavity of the liposome, in particular the nPLV of the invention. A unilamellar nPLV consists of one peripheral bilayer surrounding the central cavity whereas a multilamellar nPLV consists of more than 2 peripheral bilayers. Paucilamellar nPLV, which can be considered as a sub-class of the multilamellar nPLV, consists of 2 to 8 peripheral bilayers.

The molecular bilayers of nPLVs have a physical structure similar to classical phospholipid bilayers. For example, it has been shown that X-ray diffraction of $C_{16}$ (PEG)$_2$ ether vesicles showed a simple and principal reflection, representing the thickness of a hydrated, double layer (5.8-6.1 nanometers) of amphiphile, with smaller spacing at higher cholesterol levels—fully analogous to phospholipid bilayers. The spacing of 6.1 nanometers corresponds to the maximum extension of two amphiphile molecules plus a layer of bound water (Mitchell, et al. 1983; Adam et al. 1984). Lantzsch et al. (1996) used fluorescent transfer techniques to determine the surfaces of surfactant type $C_{12}$ (PEG)$_N$ in 1-palmitoyl-2-oleoyl phosphatidylcholine/$C_{12}$ (PEG)$_{1-8}$ liposomes. For N=1-3, the expansion of surface is equivalent to a liquid-crystalline hydrocarbon phase per molecule of $C_{12}$ (PEG)$_n$. For N=4-8, the surface area per molecule of surfactant increased gradually, suggesting a rolled up configuration of the incorporated molecules, with two water molecules per ethylene glycol segment. Further, aqueous dispersions of 1,2-tetradecyl or 1,2-hexadecyl phosphatidylcholine accept large proportions of $C_{16}$ $(PEG)_4$ (Madler et al., 1998).

As used herein, the terms "to interact" and "interacting" are meant as having an effect one on another either by direct contact or at distance. In the present invention, the agent that enhances the lipid exchange, as described, acts by contacting or colliding the nPLV of the invention with the enveloped virus or shuttling between the nPLV of the invention and the enveloped virus.

Examples of enveloped virus families and some trains within the families comprise, but are not limited to, Poxyiridae, e.g. vaccinia and smallpox, Iridoviridae, Herpesviridae, e.g. Herpes simplex, Varicella virus, cytomegalovirus and Epstein-Barr virus, Flaviviridae, e.g. Yellow fewer virus, tick-borne encephalitis virus and hepatitis C virus, Togaviridae, e.g. Rubella virus and Sindbis virus, Coronaviridae, e.g. Human coronavirus (SARS virus), Paramyxoviridae, e.g. Parainfluenza viruses, mumps virus, measles virus and respiratory syncitial virus, Rabdoviridae, e.g. vesicular stomatitis virus and rabies virus, Filoviridae, e.g. Marburg virus and Ebola virus, Orthomyxoviridae, e.g. Influenza A and B viruses, Bunyaviridae, e.g. Bwamba virus, California encephalitis virus, sandfly fever virus and Rift Valley fever virus, Arenaviridae, e.g. LCM virus, Lassa virus and Junin virus, Hepadnaviridae, e.g. hepatitis B-virus, and Retroviridae, e.g. HTLV and HIV.

Preferably, the virus of the invention is selected from Table 1.

TABLE 1

| | Family | Typical Members | Human Diseases |
|---|---|---|---|
| RNA VIRUSES | Togaviridae | Sindbis virus, Rubella virus | Easter equine encephalitis, Rubella |
| | Flaviviridae | Yellow fever virus, HCV | Japanese encephalitis, Dengue, Yellow fever, Tickborne encephalitis, Hepatitis C |
| | Orthomyxoviridae | Influenza viruses | Human Flu, Avian Flu |
| | Paramyxoviridae | NDV, Measles virus, Mumps virus, Human Metapneumovirus, RSV | Respiratory infections, Measles, Mumps |
| | Rhabdoviridae | VSV, Rabies virus | Rabies, various infections |
| | Bunyaviridae | Hantaan virus, Crimean-Congo Hemorrhagic fever virus, Rift Valley fever virus | Various hemorrhagic fevers, Rift Valley fever |
| | Coronaviridae | SARS virus | Many respiratory infections, including SARS |
| | Arenaviridae | LCMV | Lymphocytic choriomeningits |
| | Retroviridae | HTLV, HIV | Human T-cell leukemia, AIDS |
| | Filoviridae | Marburg and Ebola viruses | Marburg and Ebola hemorrhagic fevers |
| DNA VIRUSES | Herpesviridae | Human Herpes viruses, EBV, CMV |

TABLE 2-continued

| Classification | Hydrocarbon Chain | Bond | Head Group |
|---|---|---|---|
| 8. Ethoxylated glycerol fatty acid ester | $C_{16}$-$C_{18}$ (0 unsaturation) | —CO—O | —$CH_2$CHOHCH$_2$O(CH$_2$CH$_2$O)$_9$H |
| 9. Fatty acid diethanolamide | $C_{12}$-$C_{20}$ (0-2 unsaturations) | —CO—N | —(CH$_2$CH$_2$OH)$_2$ |
| 10. Fatty acid dimethyl amide | $C_{12}$-$C_{20}$ (0-2 unsaturations) | —CO—N | —(CH$_3$)$_2$ |
| 11. Faty acid sarcosinates | $C_{12}$-$C_{18}$ (0 unsaturation) | —CO—N(CH$_3$)— | —CH$_2$—COOH |
| 12. "Alkyd" | $C_{10}$ (0 unsaturation) | —O—CO | —C$_6$H$_4$—COO$^-$ |
| 13. "Alkyd" | $C_{12}$-$C_{18}$ (0-4 unsaturations); $C_{12}$-$C_{18}$ (0-4 unsaturations) | —CO—O; —CO—O | —CH$_2$— ; —(CH$_2$)$_2$—O—CO—C$_6$H$_3$(COO$^-$)$_2$ |

Most preferably, the non phospholipids of the invention are selected from the group comprising polyoxyethylene cetyl ether (PCE), palmitic acid (PA), hexadecyl trimethylammonium bromide (HTAB) and oleic acid (OA), either alone or in combination.

The nPLV of the invention is characterized by the fact that it is cholesterol-free (or substantially free of cholesterol), i.e. it does not comprise cholesterol (or, respectively, only traces of cholesterol), cholesterol derivatives such as for example PEG cholesterol, ionogenic cholesterol and surface stabilizing cholesterol, beta-sitosterol, ergosterol and phytosterol. In order to facilitate the lipid exchange between the membrane of an enveloped virus and the nPLV it is essential that cholesterol be substantially absent from the composition of the liposome.

It has been shown that membrane lipids, especially cholesterol, can exchange between phospholipids liposomes or between liposomes and cellular membranes. This occurs through a collision-activation mechanism, with kinetics, for cholesterol, in the order of seconds or minutes (Steck et al., 2002; John et al., 2002). Surprisingly, applicants have shown that lipid modifications occur through the transfer, rapidly and at a high rate, of cholesterol and possibly sphingolipids between the viral particles and the liposomes of the invention.

Surprisingly, the Applicants have shown that the composition of the invention is able to inactivate enveloped viruses. This inactivation is mediated through a lipid exchange that occurs between the nPLV and the membrane of the enveloped virus (EV).

EV lipids are synthesized by the host cell, but are deposited in the envelopes at proportions differing from that of the host cell plasma membrane. For example, the envelope of HIV is enriched in cholesterol (2.5 times) and in sphingomyelin (3 times), both located mainly in the external lamella of the envelope (Aloia, et al 1993.) The membranes of influenza viruses are similarly enriched (Scheiffele, et al 1999) and the same pattern has been reported for other EVs. Indeed, strong evidences indicate that the envelopes of all enveloped viruses contain micro-domains, called "lipid rafts", enriched in cholesterol and sphingolipids embedded in a lipid bilayer continuum. The generation of EVs particles occurs selectively from lipid rafts. Importantly, cholesterol depletion blocks EV infectivity (Moore et al 1978, Ono and Freed, 2001; Simons and Ehehalt, 2002) suggesting that viral envelope lipids may be a prime target for the arsenal against enveloped viruses.

Being non-covalently bound, cholesterol and some other lipids can exchange between cellular, EV membranes and liposomes (e.g. Moore et al, 1978, Nussbaum, Lapidot and Loyter, 1987). McLean and Phillips (1981) point out that the short "half-time", $T_{1/2}$, 2-3 min, of cholesterol transfer between phospholipid liposomes indicates collisions between these particles. Steck et al (2002) have shown that all the cholesterol transfer from red cell membranes to an acceptor molecule occurs with a $T_{1/2}$~1 sec, depending only of the concentration of the acceptor. They propose an "activation-collision" mechanism, where cholesterol is captured by collision between the membrane surface and acceptors. The $T_{1/2}$ for the transfer of a fluorescent analogue of sphingomyelin (~21 sec) between membranes is also rapid (Bai and Pagano, 1997). In contrast, the $T_{1/2}$ for the transfer of phosphatidylcholine between liposomes was measured to be ~48 h at 37° C. (McLean and Phillips, 1981).

The composition of the invention is also characterized by the fact that it comprises, besides the at least one nPLV, an agent that enhances and/or catalyses the lipid exchange between said nPLV and the membrane of an enveloped virus. Applicants have also shown that such an agent can selectively extract cholesterol from cellular membranes enhances the lipid exchange between nPLV and the membrane of EV. Preferably, this agent is a cyclodextrin or a steroidogenic acute regulatory protein (StAR). Most preferably, the agent is a cyclodextrin or a derivative thereof.

Cyclodextrins (CDs) are cyclic oligomers of glucose that can form water-soluble inclusion complexes with small molecules and portions of large compounds. Chemically they are cyclic oligosaccharides containing at least 6 D-(+) glucopyranose units attached by α-(1,4) glucosidic bonds. There are 3 natural CDs, α-, β-, and γ-CDs, which differ in their ring size and solubility. These biocompatible, cyclic oligosaccharides do not elicit immune responses and have low toxicities in animals and humans. Cyclodextrins are used in pharmaceutical applications for numerous purposes, including improving the bioavailability of drugs. β-CD can selectively extract cholesterol from cellular membranes. At high concentrations it also depletes cholesterol from viruses' envelope and reduces the viral infectivity. However, high concentrations of β-CD show cellular toxicity and can induce either cell lysis or cellular cell death (apoptosis).

Derivatives of CD are disclosed in U.S. Pat. No. 5,760,017 (inventors: Djedaini-Pilard et al.) and International Application WO91/13100 (inventors: Coates et al.), the disclosure of which is also incorporated herein by reference. Examples of CD derivatives comprise, but are not limited to dimethyl-β-cyclodextrin, trimethyl-β-cyclodextrin, randomly methylated-β-cyclodextrin, hydroxyethyl-β-cyclodextrin, 2-hydroxypropyl-β-cyclodextrin, 3-hydroxypropyl-β-cyclodextrin, 2,3-dihydroxypropyl-β-cyclodextrin, 2-hydroxyisobutyl-β-cyclodextrin, sulphobutylether-β-cyclodextrin, glucosyl-β-cyclodextrin and maltosyl-β-cyclodextrin.

Usually, the agent is added to the composition. To this end a suitable concentration of CD is prepared in water or PBS and added to the composition so as to obtain the required concentration.

Preferably, the concentration of cyclodextrin or cyclodextrin derivatives in the composition of the invention is between 0.01 mM and 50 mM. Most preferably, this concentration is between 0.1 mM and 10 mM. At such a low concentration, β-CD has limited effect on cellular integrity or viral infectivity, yet it efficiently catalyses the transfer of cholesterol from the viruses' membrane to the nPLVs.

Figure 2:
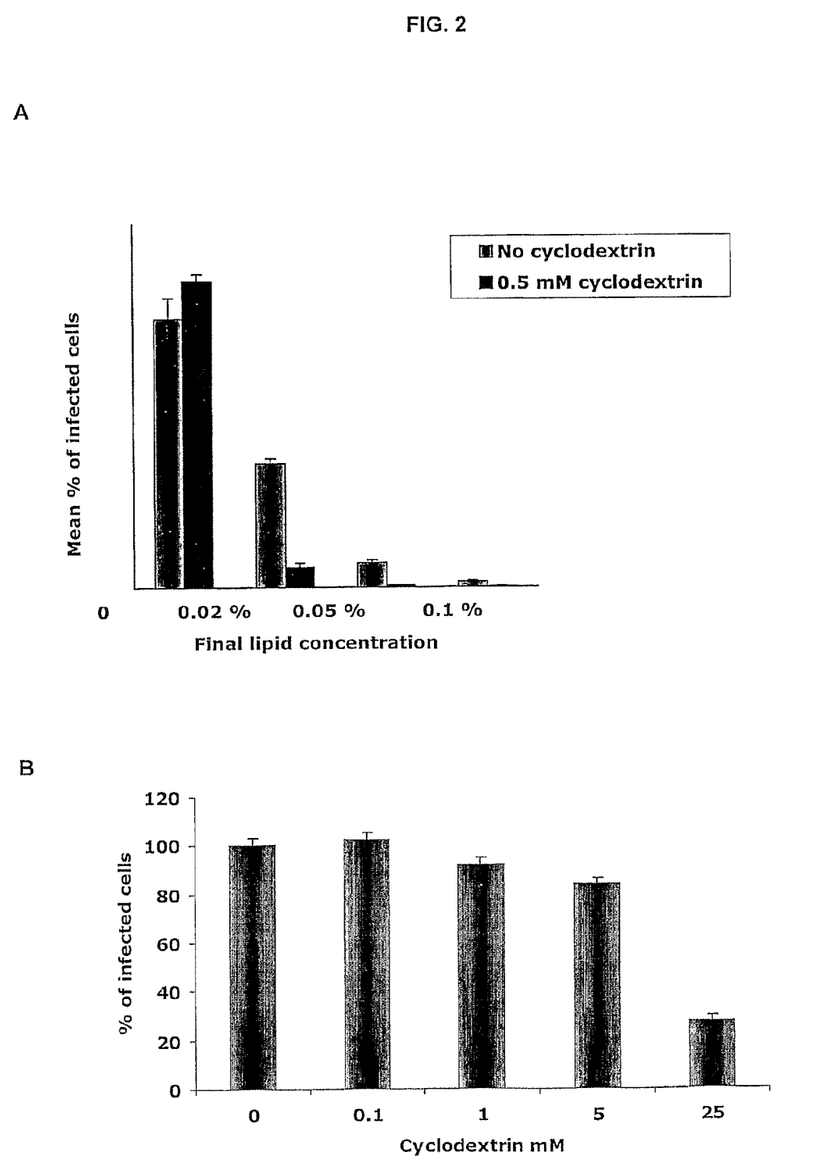

Results shown in FIG. 2 A indicate a strong synergistic effect of β-cyclodextrin on the inactivation of an enveloped virus, especially with highly diluted nPLVs concentrations.

Alternatively, the agent that enhances the lipid exchange between said nPLV and the membrane of an enveloped virus can be the steroidogenic acute regulatory protein (StAR). The steroidogenic acute regulatory (StAR) protein is an essential component in the regulation of steroid biosynthesis in adrenal and gonadal cells through cAMP-dependent pathways. In many cases transcriptional induction by cAMP is mediated through the interaction of a cAMP response-element binding protein (CREB) family member with a consensus cAMP response element (CRE; 5'-TGACGTCA-3') found in the promoter of target genes (Pulak R. Manna et al. (2002), Molecular Endocrinology 16 (1): 184-199).

A truncated form of the StAR (e.g., N62 StAR; Tuckey et al., 2002 and Alpy et al., 2005) is also envisioned for use as an agent that enhances the lipid exchange between the nPLV and the membrane of an enveloped virus. This truncated form of StAR has been shown enhancing the cholesterol transfer between phospholipid-liposomes by a factor of 5 to 10 times.

Preferably, in such as case the StAR protein is also in solution in the composition.

The composition may be in a liquid, solid (such as powder . . . ), or semi solid state.

Usually, the nPLV of the composition has a diameter comprised between 0.2 μm to 10 μm.

Generally, the lipid exchange essentially consists in the exchange of cholesterol and/or sphingolipids.

Sphingolipids are a class of lipids derived from the aliphatic amino alcohol sphingosine. The sphingosine backbone is O-linked to a (usually) charged head group such as ethanolamine, serine, or choline. The backbone is also amide-linked to an acyl group, such as a fatty acid. Sphingolipids are often found in neural tissue, and play an important role in both signal transmission and cell recognition. There are three main types of sphingolipids: ceramides, sphingomyelins, and glycosphingolipids, which differ in the substituents on their head group. Ceramides are the simplest type of sphingolipid. They consist simply of a fatty acid chain attached through an amide linkage to sphingosine. Sphingomyelins have a phosphorylcholine or phosphoroethanolamine molecule esterified to the 1-hydroxy group of a ceramide. Glycosphingolipids are ceramides with one or more sugar residues joined in a β-glycosidic linkage at the 1-hydroxyl position. Glycosphingolipids may be further subdivided into cerebrosides and gangliosides. Cerebrosides have a single glucose or galactose at the 1-hydroxy position, while gangliosides have at least three sugars, one of which must be sialic acid. Sphingolipids are commonly believed to protect the cell surface against harmful environmental factors by forming a mechanically stable and chemically resistant outer leaflet of the plasma membrane lipid bilayer. Certain complex glycosphingolipids were found to be involved in specific functions, such as cell recognition and signaling. The first feature depends mainly on the physical properties of the sphingolipids, whereas signaling involves specific interactions of the glycan structures of glycosphingolipids with similar lipids present on neighboring cells or with proteins.

Preferably, the sphingolipids of the invention are sphingomyelins or derivatives thereof.

Also in the scope of the present invention is a method for inactivating an enveloped virus comprising the step of interacting said enveloped virus to the composition of the invention allowing said nPLV of the composition and said enveloped virus to exchange their lipids.

Methods of manufacturing these vesicles, and the vesicles themselves, are described in more detail in U.S. Pat. Nos. 4,911,928 , 5,147,723 , 5,032,457, 4,895,452 and U.S. patent application Ser. No. 761,253, the disclosures of which are all incorporated herein by reference.

Also encompassed by the present invention is a pharmaceutical composition characterized in that it comprises a pharmaceutically amount of the composition of the invention, optionally in combination with one or more pharmaceutically acceptable carriers.

The phrase "pharmaceutically acceptable" refers to molecular entities and compositions that are physiologically tolerable and do not typically produce an allergic or similar untoward reaction, such as gastric upset, dizziness and the like, when administered to a human.

Acceptable carriers, excipients, or stabilizers are non-toxic to recipients, at the dosages and concentrations employed, and include buffers such as phosphate, citrate, and other organic acids; antioxidants including ascorbic acid and methionine; preservatives (such as octadecyldimethylbenzyl ammonium chloride; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes.

The form of administration of the pharmaceutical composition may be systemic or topical. For example, administration of such a composition may be various parenteral routes such as subcutaneous, intravenous, intradermal, intramuscular, intraperitoneal, intranasal, transdermal, buccal routes, preferentially by inhalation, or via an implanted device, and may also be delivered by peristaltic means.

The pharmaceutical composition, as described herein, may also be incorporated or impregnated into a bioabsorbable matrix, with the matrix being administered in the form of a suspension of matrix, a gel or a solid support. In addition the matrix may be comprised of a biopolymer.

In case the formulations to be used for in vivo administration must be sterile, this is readily accomplished for example by using sterile compounds for the preparation of the composition of the invention.

It is understood that the suitable dosage of the pharmaceutical composition of the present invention will be dependent upon the age, sex, health, and weight of the recipient, kind of concurrent treatment, if any and the nature of the effect desired.

The appropriate dosage form will depend on the disease, the nPLV, the enhancer agent and the mode of administration; possibilities include a spray or other aerosol means of delivery to the respiratory passages which is particularly effective for dealing with influenza and other viruses infecting these passages. Other ways of topically applying the inactivating solution include creams, mouthwashes, dental pastes, eye drops, solutions, ointments, gels such as vaginal gels, and lubricants such as condom lubricants. These latter categories are particularly effective for use against retroviruses such as the HIV virus.

The present disclosure also provides a method of treating or preventing a disease associated with an enveloped virus in a subject comprising the step of delivering to said subject the pharmaceutical composition as described herein, to a location proximate to said enveloped virus. Again possibilities include a spray or other aerosol means of delivery to the respiratory passages, creams, mouthwashes, dental pastes, solutions, ointments, gels such as vaginal gels, eyes drops and lubricants such as condom lubricants.

Interaction of the composition of the invention with enveloped viruses in the airways, deranges the viral membrane envelope and blocks viral infectivity, thereby, propagation in the lungs (individual prophylaxis-treatment). Physiological processes flush out the composition and inactivated viruses. Moreover, being partially or completely inactive, viruses are limited in their spread in the surrounding population when expelled by coughing or sneezing (population prophylaxis).

The terms “treating or preventing” refer to both therapeutic treatment and prophylactic or preventative measures. Those (subjects) in need of treatment include those already with the disorder as well as those in which the disorder is to be prevented. Hence, the subject to be treated herein may have been diagnosed as having the disorder or may be predisposed or susceptible to the disorder.

Preferably, the subject is an animal or a human.

Most preferably the term animal refers to domestic and farm animals (e.g. poultries), and zoo, sports, or pet animals, such as dogs, horses, pigs, cats, cows, monkeys etc. . . .

Embraced by the scope of the present invention is also the use of the pharmaceutical composition, as described herein, in the preparation of a medicament for the treatment or prevention of an enveloped virus-associated disease.

Also encompassed in the present invention is the use of the composition of the invention in the preparation of a large-scale biocompatible disinfectant. Accordingly, the composition of the invention is diluted as needed to prepare simple aqueous suspensions or dispersions in hydrogels.

The present disclosure also provides the use of the composition of the invention, in the preparation of a coating agent. This coating agent may then be used to cover, for example, surgical glows, male condoms and personal mask.

Another subject matter of the present invention is to provide a kit for inactivating an enveloped virus, said kit comprising the composition of the invention, optionally with reagents and/or instructions for use.

The kit of the present invention may further comprise a separate pharmaceutical dosage form comprising an additional anti-viral agent selected from the group comprising those described in Table 3, and combinations thereof.

Alternatively, the composition of the invention may further comprise an additional anti-viral agent selected from the group comprising those described in Table 3, and combinations thereof. Preferably, the additional anti-viral agent is selected from the anti-influenza virus group comprising Amantadine, Rimantadine, Zanamivir and Oseltamivir.

TABLE 3

| Approved antiviral drugs (Q4 2004) |
|---|
| HIV infections |
| Nucleoside Reverse Transcriptase Inhibitors NRTIs: |
| Zidovudine; Didanosine; Zalcitabine; Stavudine; Lamivudine; Abacavir; Emtricitabine. |
| Nucleotide Reverse Transcriptase Inhibitors (NtRTIs): |
| Tenofovir disoproxil. |
| Non-Nucleoside Reverse Transcriptase Inhibitors (NNRTIs): |
| Nevirapine; Delavirdine; Efavirenz. |
| Protease Inhibitors (PIs): |
| Saquinavir; Ritonavir; Indinavir; Nelfinavir; Amprenavir; Lopinavir; Atazanavir. |
| Fusion Inhibitors (FIs): |
| Enfuvirtide. |
| HBV infections |
| Lamivudine; Adefovir dipivoxii. |
| HCV infections |
| INF-α; Ribavirin. |
| HSV and VZV infections |
| Acyclovir (oral: Valaciclovir); Penciclovir (oral: Famciclovir); Idoxuridine; Trifluridine; Brivudin. |
| CMV infections |
| Ganciclovir (oral: valganciclovir); Foscarnet; Cidofovir; Formivrisen. |
| Influenza virus infections |
| Amantadine; Rimantadine; Zanamivir; Oseltamivir. |
| HIV: Human Immunodeficiency Virus; HBV: Human Hepatitis B Virus; HCV: Human Hepatitis C Virus; HSV: Herpes Simplex Virus; VZV: Varicella-Zoster Virus; CMV: Cytomegalovirus |

Source: De Clercq, *Nat. Rev. Microbio.* (2004) 2: 704-720.

Generally, the Kit comprises a container and a label or package insert on or associated with the container. Suitable containers include, for example, bottles, vials, syringes, etc. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle or an aerosol spray device). The label or package insert indicates that the composition is used for treating the condition of choice, such as viral infections.

Alternatively, or additionally, the Kit may further comprise a second (or third) container comprising a pharmaceutically acceptable buffer, such as bacteriostatic water for injection (BWFI), phosphate-buffered saline, Ringer’s solution and dextrose solution. It may further include other materials desirable from a commercial and user standpoint, including other buffers, diluents, filters, needles, and syringes.

Those skilled in the art will appreciate that the invention described herein is susceptible to variations and modifications other than those specifically described. It is to be understood that the invention includes all such variations and modifications without departing from the spirit or essential characteristics thereof. The invention also includes all of the steps, features, compositions and compounds referred to or indicated in this specification, individually or collectively, and any and all combinations or any two or more of said steps or features. The present disclosure is therefore to be considered as in all aspects illustrated and not restrictive, the scope of the invention being indicated by the appended Claims, and all changes which come within the meaning and range of equivalency are intended to be embraced therein.

Various references are cited throughout this Specification, each of which is incorporated herein by reference in its entirety.

The foregoing description will be more fully understood with reference to the following Examples. Such Examples, are, however, exemplary of methods of practicing the present invention and are not intended to limit the scope of the invention.

EXAMPLES

Example 1

Material And Methods
Cells and Viruses.

MK2 (monkey) cells were grown at 37° C. in DMEM containing 5% of bovine serum albumin (BSA) until they reached 70% of confluence.

Two recombinant Sendai viruses were used: 1) rSeV-Luc, which encodes the *Photinus pyralis* luciferase gene as a marker; and 2) rSeV-GFP, which encodes the *Aequora victoria* green fluorescent protein as a marker.
nPLVs Preparation.

The primary lipid used was polyoxyethylene cetyl ether (PCE), either alone or in combination with palmitic acid (PA) or with hexadecyl trimethylammonium bromide (HTAB) at the indicated molar ratio.

The lipid mixture was heated to 50° C. and mixed with phosphate buffer saline (PBS), also pre-heated to 50° C., using the 2-syringes method. Briefly, a 10-ml syringe, containing 0.5 g of the lipid mixture, was connected to a second 10-ml syringe containing 10 ml of phosphate buffer saline (PBS) (5% final lipid concentration). The lipid blend was then injected into the PBS syringe, and the resulting mixture was rapidly passed forth and back about 20 times, until a homogeneous suspension was obtained. The preparation was subsequently checked for nPLV quality by phase-contrast microscopy.
Inactivation Assay.

The nPLV preparations were diluted in PBS to the indicated concentrations. The diluted nPLVs were then mixed with the viruses in a final volume of 100 µl. The virus-nPLV mixtures were incubated at room temperature for 30 minutes with shaking. Virus concentrations ranged from $10^5$ to $2\times10^6$ particles.

Following incubation, the mixtures were diluted to 500 ml in DMEM without BSA and directly added onto cells. Infections were performed at 33° C. for one hour, and then infectious mixes were removed. Cells were washed once with DMEM without BSA, 10 ml of DMEM with 1% BSA were added and incubation was further performed at 37° C. for 36 hours.

Experiments were done in triplicates.
Monitoring.

For rSeV-Luc infections, cells were lysed and luciferase activity was determined using the Promega's Luciferase Assay System. Measurements were done with TD-20/20 luminometer (Turner Designs).

For rSeV-GFP infections, cells were harvested by trypsinization and submitted to FACS analysis using a FACS scan machine.

Example 2

Synergistic Effect of Cyclodextrin

Cells and Virus.

MK2 (monkey) cells were grown at 37° C. in DMEM containing 5% of bovine serum albumin (BSA) until they reached 70% of confluence.

A recombinant Sendai virus was used, rSeV-Luc, which encodes the *Photinus pyralis* luciferase gene.
nPLVs Preparation.

As previously described in example 1.
Inactivation Assay.

The nPLV preparations were diluted in PBS to the indicated concentrations. The diluted nPLVs were then mixed with the viruses, either alone (no cyclodextrin) or in combination with 0.5 mM (final concentration) of cyclodextrin, in a volume of 100 µl. The virus-nPLV mixtures were incubated at room temperature for 20 minutes with shaking. About $10^5$ viral particles were used.

Following incubation, the mixtures were diluted to 500 ml in DMEM without BSA and directly added onto cells. Infections were performed at 33° C. for one hour, and then infectious mixes were removed. Cells were washed once with DMEM without BSA, 10 ml of DMEM with 1% BSA were added and incubation was further performed at 37° C. for 36 hours. Experiment was done in duplicates.
Monitoring.

MK2 cells were lysed and luciferase activity was determined using the Promega's Luciferase Assay System. Measurements were done with TD-20/20 luminometer (Turner Designs).

Example 3

Results

In order to explore the possibility of inactivating enveloped viruses (EVs) through lipid modification of their envelope, Applicants used Sendai virus (SeV) as a model. SeV is an enveloped virus of the Paramyxoviridae family and has genetic and structural similarities with several human pathogenic viruses. It is a respiratory virus whose natural host is the mouse, but it can be grown in a wide range of eukaryotic cells, including embryonated chicken eggs in which high-titer viral stocks can easily be obtained. Similarly to many EVs, SeV has been shown to have cholesterol dependence for its infectivity, although the precise mechanism is not fully clarified yet. Applicants used 2 types of recombinant SeV (rSeV) having different marker gene encoded in their genomes. With rSeV-Luc, encoding the luciferase gene, the level of infection can be monitored using a very sensitive biochemical assay. rSeV-GFP, in turn, encodes the green fluorescent protein gene and infection can be followed at the cellular level using Fluorescence-Associated Cell Sorting (FACS), an assay allowing to precisely determining the number of infected cells.

Applicants synthesized 3 types of nPLVs using different lipid compounds: 1) nPLVs composed of a neutral (uncharged) component alone, polyoxyethylene cetyl ether (PCE). 2) nPLVs composed mainly of PCE but including 0.1% mol of palmitic acid (PA), a negatively charged lipid. 3) nPLVs composed of PCE and 0.1% mol of hexadecyl trimethylammonium bromide (HTAB), a positively charged lipid.

Figure 1:
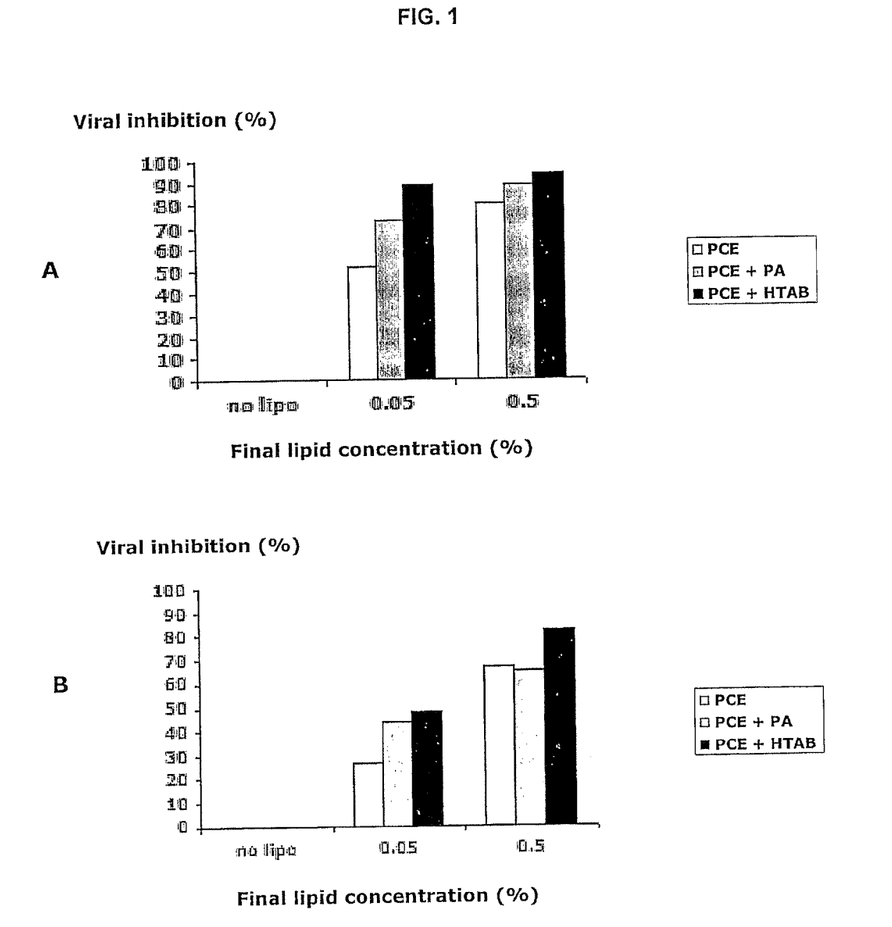
FIG. 1 shows the effect of different nPLVs compositions on the inactivation of 2 different recombinant Sendai viruses: A) rSeV-Luc, expressing the luciferase gene and B) rSeV-GFP, expressing the green fluorescent protein. PCE: polyoxyethylene cetyl ether, PA: palmitic acid, HTAB: hexadecyl trimethylammonium bromide.

As evident from FIG. 1, the efficiency of viral inactivation differs greatly depending on nPLV lipid composition. These variations are observed with both recombinant viruses in a very similar range. It is clear from these results that the presence of an electric charge, either positive or negative, at the surface of the nPLVs improves drastically the viral inactivation. This can be explained at 2 levels. First, electrostatic repulsion between the nPLVs might avoid vesicles coalescence, aggregation or fusion, thus improving the quality and stability of the nPLVs preparation. Second, due to its phospholipid composition and to the presence of surface glycoproteins, it is likely that the surface of a viral particle is charged at physiological pH. The presence of local charged micro domains on the viral particle surface might favor interactions with charged nPLVs through electrostatic attraction.

β-cyclodextrin is a pharmaceutical agent well known for its ability to extract cholesterol from cellular phospholipid membranes. However, the range of concentrations used in most in vitro experiments (50-100 mM) is detrimental for cellular integrity and can induce cell death. Applicants therefore decided to investigate whether very low concentrations of β-cyclodextrin could be used to improve cholesterol transfer from viral particles to nPLVs. The rationale behind these experiments is the following: at very low concentrations (0.5-2 mM) β-cyclodextrin will not exert its cellular toxicity effect, yet it will be able to extract cholesterol from the viral lipid raft domains. Once loaded with cholesterol β-cyclodextrin will shuttle to the nPLVs and deliver cholesterol to the non-phospholipid membranes. The empty β-cyclodextrin will then continue the extraction cycle until cholesterol concentration equilibrium is reached between nPLVs and viral particles. Thus, at such a low concentration b-cyclodextrin will serve as a catalyst of the cholesterol transfer between viral envelopes and nPLVs. FIG. 2A clearly shows that β-cyclodextrin at a concentration of 0.5 mM greatly enhances the viral inactivation by nPLVs composed of PCE with 0.1% mol of oleic acid (OA), a negatively charged lipid. As shown in FIG. 2B, this enhancing activity is due to the catalysing activity because a direct effect of β-cyclodextrin alone on the viral particles is only observed at concentration higher than 5 mM.

REFERENCES

Adam C D, Durrant, J A, Lowry M R, Tiddy G. J. Gel and liquid-crystal Phase structures of the trioxyethyleneglycol monohexadecyl ether/water system. J. Chem. Soc. Faraday Trans 1984; 80:789-01.

Aloia, R C, Tian H, Jensen F C. Lipid composition and fluidity of the human immunodeficiency virus envelope and host cell plasma membranes, Proc. Natl. Acad Sci 1993; 90:5181-85

Bai, J. and R. E. Pagano, Measurement of spontaneous transfer and transbilayer movement of BODIPY-labeled lipids in lipid vesicles. Biochemistry 1997; 36:8840-48.

Brahmbhatt M. Avian influenza: Economic and social impacts. http:web.worldbank.org Bright R A, Medina M-J, Xu X, Perez-Oronoz G, Wallis T A, Davis X M, Povinelli L, Coc N J, Kimov A. Incidence of adamantine resistance among influenza A (H3N2) viruses isolated worldwide from 1994 to 2005; a cause for concern. 2005. Lancet DOL: 10.1016/50140-6736. September 22. pg 1-7

El Baraka M, Pecheur E I, Wallach D F H, Philippot J R. Non-phospholipid fusogenic liposomes. Biochim. Biophys. Acta 1996; 1280, 107-114.

Greenberg M and Cammack N. Resistance to enfurvirtide the first HIV fusion inhibitor. 2004. J. Antimicrobial Chemotherapy 54; 333-40.

Heerklotz H. Triton promotes domain formation in lipid rafts. Biophys J 2002; 83: 2693-701.

Hersberger M, Nusbaumer C, Scholer A, Knöpfli V, Eekardstein A V. Influence of practicable virus inactivation procedures on tests for frequently measured analytes in plasma. Clin Chem 2004; 50; 944-46.

HIV/AIDS and work: global estimates, impact and response 2004; ILO Programme on HIV/AIDS and the world of work.

Jefferson T, Rivetti D, Rivetti A, Rudin M, Pietrantonj C D, Demichelli V. Efficacy and effectiveness of influenza vaccines in elderly people: a systematic review. Lancet DOL 1016/50140-.

Kilby J. M., Enron J. J. Mechanisms of disease. Novel therapies based on mechanisms of HIV-1 cell entry. New Engl J Med, 2003; 48: 2228-38.

Lantzsch G, Binder F L Heerklotz H, Wendling M. Klose W. Surface areas and packing constraints in POPC/$C_{12}EO_n$ membranes; a time-resolved fluorescence study. Biophys Chem, 1996; 58: 289-02.

McLean L R, Phillips M. C. Mechanism of cholesterol and phosphatidylcholine exchange or transfer between unilamellar vesicles. Biochemistry 1981; 12: 2893-90.

Mitchell J, Tiddy, G J T, Waring, L, Bostock T, McDonald M. P. Phase behavior of polyoxyethylene surfactants with water. J. Chem. Soc. Faraday Trans 1983, 79:975-1000.

Moscona. A. NANASE Inhiibitors for influenza. New. Engl. J. Med. 2005:353; 1363-73.

Mukherjee S, Chattopadhyay A., Membrane organization at low cholesterol concentrations: a study using 7-nitrobenz-2-oxa-1,3-diazol-4-yl-labelled cholesterol. Biochemistry. 1996; 35:1311-22.

Ono A, Freed E. O. Plasma membrane rafts play a critical role in HIV-1 assembly and release. Proc Natl Acad Sci 2001; 98: 13925-30.

Pelet T, Miazza V, Mottet G, Roux L. High throughput screening assay for negative single stranded rna virus polymerase inhibitors. J Virol Methods 2005; 128:1-2; 29-36.

Rockstroh J K Mauss S. Clinical perspective of fusion inhibitors for treatment of HIV. 2004. J. Antimicrobial Chemotherapy 54:700-702.

Roberts P. Resistance of vaccinia virus to inactivation by solvent/detergent treatment of blood products. Biologicals 200; 28:29-32.

Rousso I, Mixon M B, Chen B K, Kim P S. Palmitoylation of the HIV-1 envelope glycoprotein is critical for viral infectivity. Proc Natl Acad Sci 2000; 97:1353-25.

Scheiffele P, Rietveld A, Wilk T, Simons K. Influenza viruses select ordered lipid domains during budding from the plasma membrane, J Biol Chem, 1999; 274:2038-44.

Simons K, Ehehalt R. Cholesterol, lipid rafts and disease, J Clin Invest 2002; 110:597-03.

Small D J. Role of ABC transporters in secretion of cholesterol from liver to bile. Proc Natl Acad Sci 2002; 100:4-7.

Steck T L, Straus J H, Wallach D. F. H. A model for the behavior of vesicles in density gradients: Implications for fractionation. Biochim Biophys. Acta 1970; 23:385-93.

Steck T L, Ye J, Lange Yvonne. Probing red cell membrane cholesterol movement with cyclodextrin; Biophys J 2000; 283:2118-25.

Tashima K T, Carpenter C. C. J. Fusion Inhibition—A major but costly step forward in the treatment of HIV-1. N Engl J Med. 2003; 348:2249-22.

Taubenberger J K, Reid A H, Lourens R M, Wang R, Jin G, Fanning T G. Characterization of the 1918 influenza virus polymerase genes. 2005. Nature 437/6:889-93.

Tumpey, T T, Basler C F, Aguillar P V, Zeng H, Solorzano A, Swayne D E, Cox N J, Katz J M, Characterization of the reconstructed 1918 Spanish influenza pandemic virus. 2005. Science; 310:77-80.

Varanelli C, Kumar S. Wallach D. F. H. 1996, Method of inhibiting viral reproduction using nonphospholipid vesicles. U.S. Pat. No. 5,561,062

Wallach D F H 1990a, Lipid vesicles formed of surfactants and steroids. U.S. Pat. No. 4,197,951.

Wallach D F H. 1990b Paucilamellar lipid vesicles. U.S. Pat. No. 4,911,928.

Wallach D F H. 1992, Paucilamellar lipid vesicles. U.S. Pat. No. 5,147,723.

Wallach D F H. 1996, Paucilamellar lipid vesicles. U.S. Pat. No. 5,474,848

Wallach D F H., 1997, Hybrid paucilamellar lipid vesicles. U.S. Pat. No. 5,628,936.

Wallach D F H, Varanelli C., 1997, Lipid vesicle fusion as a method of transmitting a biologically active material to a cell. U.S. Pat. No. 5,665,380.

Wallach D F H 1990a, Lipid vesicles formed of surfactants and steroids. U.S. Pat. No. 4,197,951.

Wallach D F H. 1990b Paucilamellar lipid vesicles. U.S. Pat. No. 4,911,928.

Wallach D F H. 1992, Paucilamellar lipid vesicles. U.S. Pat. No. 5,147,723.

Wallach D F H. 1996, Paucilamellar lipid vesicles. U.S. Pat. No. 5,474,848

Wallach D F H., 1997, Hybrid paucilamellar lipid vesicles. U.S. Pat. No. 5,628,936.

Wallach D F H, Varanelli C., 1997, Lipid vesicle fusion as a method of transmitting a biologically active material to a cell. U.S. Pat. No. 5,665,380.

Wallach D F H New non-phospholipid vesicles (nPLV) and their use in cosmetic, therapeutic and prophylactic applications, 2001. European Patent application 1,304,103, PCT, US extension 2005.

Working committee of the World Health organisation (WHO). Avian influenza (H5N1) infection Wallach D F H New non-phospholipid vesicles (nPLV) and their use in cosmetic, therapeutic and prophylactic applications, 2001. European Patent application 1,304,103, PCT, US extension 2005.

The invention claimed is:

1. A method for inactivating an enveloped virus, said method comprising contacting an enveloped virus with an effective amount of a composition comprising
 (a) at least one cholesterol-free, non-phospholipid Lipid Vesicle (nPLV); and
 (b) between about 0.1 mM to about 10 mM of an agent selected from the group consisting of: α-cyclodextrin, β-cyclodextrin, γ-cyclodextrin, dimethyl-β-cyclodextrin, trimethyl-β-cyclodextrin, randomly methylated-β-cyclodextrin, hydroxyethyl-β-cyclodextrin, 2-hydroxypropyl-β-cyclodextrin, 3-hydroxypropyl-β-cyclodextrin, 2,3-dihydroxypropyl-β-cyclodextrin, 2-hydroxyisobutyl-β-cyclodextrin, sulphobutylether-β-cyclodextrin, glucosyl-β-cyclodextrin, maltosyl-β-cyclodextrin and a combination thereof.

2. The method of claim 1, wherein the enveloped virus is selected from the group consisting of: Sindbis virus, Rubella virus, Yellow fever virus, Hepatitis C virus, Influenza virus, Measles virus, Mumps virus, Human Metapneumovirus, Respiratory Syncytial virus, Vesicular Stomatitis virus, Rabies virus, Hantaan virus, Crimean-Congo Hemorrhagic fever virus, Rift Valley fever virus, Coronavirus, SARS virus, LCM virus, human T-cell leukemia virus, human immune deficiency virus (HIV), marburg virus, Ebola virus, human herpes viruses, vaccinia virus, Hepatitis B virus, and a combination thereof.

3. The method of claim 1, wherein the enveloped virus is selected from the group consisting of: respiratory syncytial virus, Coronavirus, SARS virus, metapneumovirus, human herpes virus, Influenza virus, HIV, Stomatitis virus, vaccinia virus, Ebola virus, and a combination thereof.

4. The method of claim 1, wherein the enveloped virus is Influenza virus or HIV.

5. The method of claim 1, wherein the agent is selected from the group consisting of β-cyclodextrin, 2-hydroxypropyl-β-cyclodextrin, dimethyl-β-cyclodextrin, trimethyl-β-cyclodextrin, randomly methylated-β-cyclodextrin, and a combination thereof.

6. The method of claim 1, wherein the agent is present in the composition at a concentration of about 0.1 mM.

7. The method of claim 1, wherein the agent is present in the composition at a concentration of about 0.5 mM.

8. The method of claim 1, wherein the agent is present in the composition at a concentration of about 1 mM.

9. The method of claim 1, wherein the agent is present in the composition at a concentration of about 5 mM.

10. The method of claim 1, wherein the agent is present in the composition at a concentration of between about 0.5 mM to about 2 mM.

11. The method of claim 1, wherein the agent enhances the lipid exchange between the nPLV and the membrane of said enveloped virus.

12. The method of claim 1, wherein the agent is 2-hydroxypropyl-β-cyclodextrin.

13. The method of claim 12, wherein the 2-hydroxypropyl-β-cyclodextrin is present in the composition at a concentration of 5 mM.

* * * * *